United States Patent
Fernandez Pena et al.

(10) Patent No.: US 10,543,174 B2
(45) Date of Patent: Jan. 28, 2020

(54) MODIFIED RELEASE TABLET COMPOSITION COMPRISING MIRABEGRON

(71) Applicant: SYNTHON B.V., Nijmegen (NL)

(72) Inventors: Agnes Fernandez Pena, Sant Boi de Llobregat (ES); Jose Velada Calzada, Nijmegen (NL); Rohit Kumar, Sant Boi de Llobregat (ES); Lisardo Alvarez Fernandez, Sant Boi de Llobregat (ES)

(73) Assignee: Synthon B.V., Nijmegen (NL)

(*) Notice: Subject to any disclaimer, the term of this patent is extended or adjusted under 35 U.S.C. 154(b) by 0 days.

(21) Appl. No.: 16/096,523

(22) PCT Filed: Apr. 21, 2017

(86) PCT No.: PCT/EP2017/059561
§ 371 (c)(1),
(2) Date: Oct. 25, 2018

(87) PCT Pub. No.: WO2017/186598
PCT Pub. Date: Nov. 2, 2017

(65) Prior Publication Data
US 2019/0133957 A1 May 9, 2019

(30) Foreign Application Priority Data
Apr. 25, 2016 (EP) .................... 16166922

(51) Int. Cl.
*A61K 9/20* (2006.01)
*A61K 31/426* (2006.01)
*A61K 31/4725* (2006.01)

(52) U.S. Cl.
CPC .......... *A61K 9/2054* (2013.01); *A61K 9/2031* (2013.01); *A61K 9/2077* (2013.01); *A61K 9/2086* (2013.01); *A61K 9/2095* (2013.01); *A61K 31/426* (2013.01); *A61K 31/4725* (2013.01)

(58) Field of Classification Search
CPC .. A61K 9/2054; A61K 9/2031; A61K 9/2077; A61K 9/2086; A61K 9/2095; A61K 31/426; A61K 31/4725
See application file for complete search history.

(56) References Cited

U.S. PATENT DOCUMENTS

| | | | |
|---|---|---|---|
| 6,346,532 B1 | 2/2002 | Maruyama et al. | |
| 8,772,315 B2 | 7/2014 | Suzuki et al. | |
| 2005/0261328 A1 | 11/2005 | Wienrich et al. | |
| 2005/0261369 A1 | 11/2005 | Mehlburger et al. | |
| 2007/0276047 A1* | 11/2007 | Oberegger | A61K 9/2027 514/649 |
| 2010/0137358 A1 | 6/2010 | Kharwade et al. | |
| 2010/0144807 A1 | 6/2010 | Takaishi et al. | |
| 2015/0224087 A1* | 8/2015 | Peddy | A61K 31/426 514/370 |
| 2015/0306090 A1* | 10/2015 | Tsutsui | A61K 31/426 424/464 |
| 2018/0016246 A1 | 1/2018 | Singh | |
| 2019/0110995 A1 | 4/2019 | Fernandez Pena et al. | |

FOREIGN PATENT DOCUMENTS

| | | |
|---|---|---|
| CN | 104352475 | 2/2015 |
| EP | 2832730 | 2/2015 |
| EP | 2 891 493 A1 | 7/2015 |
| WO | WO 94/06414 | 3/1994 |
| WO | WO 99/20607 | 4/1999 |
| WO | WO 03/039531 | 5/2003 |
| WO | WO 2004/047838 | 6/2004 |
| WO | WO 2010/038690 | 3/2012 |
| WO | WO 2015/120110 A2 | 8/2015 |
| WO | WO 2015/129893 | 9/2015 |
| WO | WO 2017/186593 | 11/2017 |

* cited by examiner

*Primary Examiner* — Doan T Phan
(74) *Attorney, Agent, or Firm* — Buscher Patent PLLC

(57) ABSTRACT

The present invention relates to a pharmaceutical composition, particularly a modified release tablet composition comprising mirabegron or a pharmaceutically acceptable salt thereof and to a process for preparing such a composition.

16 Claims, 2 Drawing Sheets

MODIFIED RELEASE TABLET COMPOSITION COMPRISING MIRABEGRON

BACKGROUND OF THE PRESENT INVENTION

The present invention relates to a pharmaceutical composition, particularly a modified release tablet composition comprising mirabegron or a pharmaceutically acceptable salt thereof and to a process for preparing such a composition.

Mirabegron and the pharmaceutically acceptable salts thereof were first disclosed in International Publication No. WO 99/20607 (Example 41).

A mirabegron containing pharmaceutical product is approved under the brand name Betmiga® in the EU and Mirbetriq® in the US as modified release tablets comprising 25 and 50 mg of mirabegron.

Mirabegron is the generic name of (R)-2-(2-aminothiazol-4-yl)-4'-[2-[(2-hydroxy-2-phenylethyl)amino]ethyl]acetic acid anilide, known as a selective β3 adrenoreceptor agonist and used as a therapeutic agent for overactive bladder, such as overactive bladder accompanied by prostatic hyperplasia, or overactive bladder accompanied by urinary urgency, urinary incontinence, and urinary frequency.

Mirabegron is considered to be a Class III compound according to the Biopharmaceutical Classification System (BCS). That means that it has high solubility and low permeability. Based on the assessment report of Betmiga® published by the European Medicines Agency, mirabegron is soluble in water between neutral to acidic pH.

It is known that the bioavailability of mirabegron is affected by the presence of food in the GI tract. Therefore to prevent this food effect, the commercially available pharmaceutical formulations of mirabegron are in the form of a modified-release (MR) tablet formulation based on an orally controlled absorption system (OCAS®) tablet formulation.

The OCAS® system is described in WO9406414 (A1). WO9406414 (A1) describes a hydrogel-type sustained-release preparation comprising (1) at least one drug (tamsulosine as one of the examples), (2) an additive which insures a penetration of water into the core of the preparation and (3) a hydrogel-forming polymer, wherein said preparation is capable of undergoing substantially complete gelation during its stay in the upper digestive tract including stomach and small intestine and is capable of releasing the drug in the lower digestive tract including colon.

Further, the concept of using a sustained release pharmaceutical composition for reducing or avoiding the changes in pharmacokinetics such as AUC or Cmax accompanied by food intake is known. It was first disclosed in WO03039531 (A1) and was applied to tamsulosin.

The application of the OCAS® system to Mirabegron is described in WO2010038690 (A1). It specifically describes a tablet formulation comprising mirabegron or a pharmaceutically acceptable salt thereof, an additive which ensures penetration of water into the pharmaceutical composition, and a polymer which forms a hydrogel.

Due to the use of said additive the preparation undergoes a substantially complete gelation in the upper part of the GI tract, namely stomach and small intestine. The formed gel matrix is then maintained in the hydrated state during the passage through the GI tract for 4 hours or more maintaining a constant release and thus reducing the effects by food, because the drug release from the formulation would become the rate-limiting step for absorption. This results in a uniform, sustained release of the drug throughout the entire GI tract independently of the presence of food.

However, there is still a need for a stable pharmaceutical composition of mirabegron or a pharmaceutically acceptable salt thereof having a bioequivalent drug release profile to the commercially available product Betmiga® and that is obtainable by a straight forward and economical process.

BRIEF DESCRIPTION OF THE PRESENT INVENTION

The present invention relates to a modified release tablet composition comprising
1. 5 to 25 wt %, with respect to the total weight, of a therapeutically effective dose of mirabegron or a pharmaceutically acceptable salt thereof;
2. 15 to 40 wt %, with respect to the total weight, of a mixture of one or more polyethylene oxides, the mixture having a viscosity of 100 to 800 preferably 400 to 800 cps at a 2% aqueous solution at 25° C.;
3. A water insoluble hydrophilic excipient.

The modified release tablet compositions of the present invention are stable and show an in vitro dissolution profile wherein mirabegron is released in at least 10%, preferably 10-50% within 3 hours, at least 30%, preferably 30 to 70% within 5 hours and at least 80% within 10 hours when the composition is subjected to a dissolution study in 900 ml phosphate buffer (pH 6.8) using a USP apparatus 1 (basket) at 100 rpm at 37° C.

The term "stable" as used herein means that tablets comply with the dissolution specification when subjected to a 6 months stability study at the accelerated stability conditions of 40° C. and 75% RH.

The term "total weight" refers to the total weight of the uncoated tablet.

DETAILED DESCRIPTION OF THE INVENTION

Figure 1:
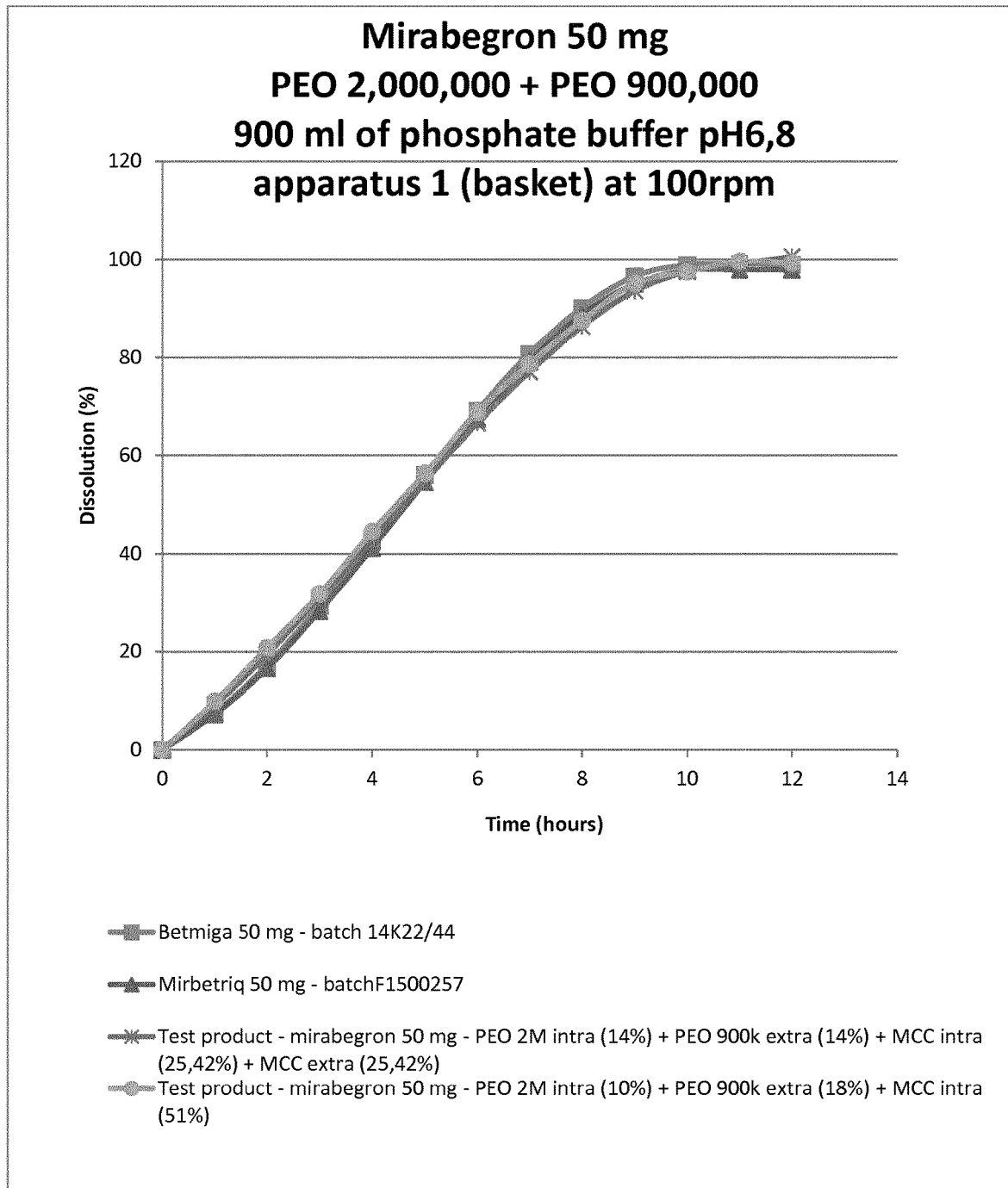
FIG. 1 shows the in vitro dissolution profile of tablet compositions in accordance with the present invention as compared to commercially available tablets.

Modified release hydrogel tablets based on polyethylene oxide tend to suffer changes in their dissolution release profile when exposed to oxygen or UV light not complying with the dissolution specifications during the stability study. This is relevant since it may cause loss of the desired therapeutic control of the modified release tablets. The polyethylene oxide is prone to degradation that occurs due to oxidation resulting in a reduction of its viscosity. In order to prevent this oxidation an antioxidant agent might be added in the formula.

Preferably the pharmaceutical tablet composition of the present invention is stabilized by an oxygen and UV light barrier like for example a primary packaging material like Aluminium/Aluminium blister foil or a light resistant HDPE container.

The modified release tablet composition of the present invention is described in further detail hereinafter.

A therapeutically effective dose of mirabegron or a pharmaceutically acceptable salt thereof is present in a weight ratio of 5 to 25% with respect to the total weight in the tablet.

In a particular embodiment mirabegron or a pharmaceutically acceptable salt thereof has a particle size distribution of D90 between 10 and 150 μm. Preferably the D90 is between 10 and 60 μm, more preferably between 20 and 50 μm.

The modified release tablet composition of the present invention further comprises 15 to 40 wt %, with respect to the total weight, of a mixture of one or more polyethylene oxides, the mixture having a viscosity of 100 to 800, preferably 400 to 800 cps at a 2% aqueous solution at 25° C.

Preferably the polyethylene oxide is a mixture of a polyethylene oxide having an average molecular weight of approximately 2,000,000 and a polyethylene oxide having an average molecular weight of approximately 900,000.

In another embodiment the polyethylene oxide 2,000,000 is present in a weight ratio of 1 to 15%, more preferred 1 to 4% with respect to the total weight and the polyethylene oxide 900,000 is present in a weight ratio of 10 to 45% more preferred 10% to 25%, even more preferred 15 to 20% with respect to the total weight.

Polyethylene oxide (Polyox WSR®) is a nonionic homopolymer of ethylene oxide, represented by the formula $[(OCH_2CH_2)n]$, in which n represents the average number of oxyethylene groups and varies from about 2,000 to 100,000; the molecular weights range from about 100,000 to 7 million. Polyethylene oxide occurs as a white to off-white, free-flowing powder. It is available in several different grades that vary in viscosity profiles in aqueous isopropyl alcohol solutions. Polyethylene oxide may be degraded by oxidation and commercially available polyethylene oxide may contain a suitable antioxidant.

Polyethylene oxide is a very hydrophilic polymer. Upon contact with an aqueous medium, it hydrates rapidly to form a gel layer on the tablet surface for the release of the active. Typically the drug release occurs by combination of two mechanisms; diffusion and erosion. For a water soluble drug substance as mirabegron, diffusion of the active through the gel layer is the dominant mechanism but gradual erosion of the gel, exposing fresh surfaces containing drug to the dissolution media, may also take place.

The modified release tablet composition of the present invention further comprises a water insoluble hydrophilic excipient (insoluble in water means more than 10,000 ml of water per gram of solute), such as microcrystalline cellulose (MCC). This water insoluble hydrophilic excipient functions as a water penetration enhancer. In a preferred embodiment the weight ratio of the water insoluble hydrophilic excipient is 40 to 70% with respect to the total weight, preferably 45 to 65% with respect to the total weight.

Examples of water insoluble hydrophilic excipients are microcrystalline cellulose, crospovidone, croscarmellose.

In a particular embodiment the water insoluble hydrophilic excipients is microcrystalline cellulose.

It is known that microcrystalline cellulose swells in water. This effect is attributed to penetration of water into the cellulose matrix as a result of pore capillary action with subsequent disruption of the hydrogen bonds holding the fibrils together.

Although the drug release is mainly controlled by the hydrogel forming polymer, such as the polyethylene oxide (PEO), the microcrystalline cellulose also affects the drug dissolution.

The proper combination between a particular viscosity and weight ratio of the hydrogel forming polymer in the presence of a water insoluble hydrophilic excipient is needed to reach the desired modified release profile.

A weight ratio of 5 to 25%, with respect to the total weight, of a therapeutically effective dose of mirabegron or a pharmaceutically acceptable salt thereof, 15 to 40 wt %, with respect to the total weight, of a mixture of one or more polyethylene oxides, the mixture having a viscosity of 100 to 800 preferably 400 to 800 cps at a 2% aqueous solution at 25° C. and a water insoluble hydrophilic excipient within the tablet core has shown good results in the achievement of the desired dissolution profile and compliance to the dissolution specification during the stability testing.

In FIG. 1, the use of microcrystalline cellulose as extragranular and/or intragranular components and its influence on drug dissolution is illustrated. The studied formulas are disclosed in Table 1, Table 2 and Table 3.

Additionally the present invention may comprise other pharmaceutically acceptable excipients, for example, binders, diluents, lubricants, glidants and antioxidants.

Binders which are suitable for use in accordance with the present invention include hydroxypropyl cellulose, povidone, dihydroxy propylcellulose, and sodium carboxyl methylcellulose, preferably hydroxypropyl cellulose. Binders are preferably used in an amount of from 1% to 6 wt % preferably 1% to 5 wt % with respect to the total weight of the composition.

Diluents are fillers which are used to increase the bulk volume of a tablet or capsule. Generally, by combining a diluent with the active pharmaceutical ingredient, the final product is given adequate weight and size to assist in production and handling.

Suitable examples of diluents to be used in accordance with the present invention include starch, pregelatinized starch, and calcium phosphate, lactose, sorbitol, mannitol and sucrose.

The tablet composition of the invention may also contain a lubricant. Lubricants are generally used in order to reduce sliding friction. In particular, to decrease friction at the interface between a tablet's surface and the die wall during ejection, and reduce wear on punches and dies. Suitable lubricants to be used in accordance with the present invention include magnesium stearate, calcium stearate, stearic acid, glyceryl behenate, hydrogenated vegetable oil, and glycerine fumarate. The tablet composition of the invention may also contain a glidant. Glidants enhance product flow by reducing interparticulate friction. A suitable example is colloidal silicon dioxide.

Lubricants and glidants preferably are used in a total amount of from 0.05% to 5 wt % with respect to the total weight.

The tablet composition of the invention may also contain an antioxidant. Antioxidants are substances added in small quantities to hydrocarbons which are susceptible to oxidation. Suitable oxidants to be used in the present invention are Butylated hydroxytoluene (BHT), butylated hydroxyanisole BHA, vitamine E, EDTA or propyl gallet. The preferred oxidant is BHT. Antioxidant are preferably used in an amount of from 0.01% to 1% preferably 0.1% to 0.5 wt % with respect to the total weight based on the total weight of the composition.

In a preferred embodiment, the tablet composition of the present invention comprises the following ingredients, based on the total weight of the composition:
  a. A therapeutically effective dose of mirabegron or a pharmaceutically acceptable salt thereof in an amount of from 5 to 25 wt % with respect to the total weight;
  b. A mixture of polyethylene oxide 2,000,000 in a weight ratio of 1 to 15%, preferably 1 to 4% with respect to the total weight and polyethylene oxide 900,000 in a weight ratio of 10 to 45%, preferably 10 to 25% with respect to the total weight the mixture Microcrystalline cellulose in a weight ratio of 40 to 70% with respect to the total weight, preferably 45 to 65% with respect to the total weight;

c. A lubricant from 0.05% to 5 wt % with respect to the total weight;

d. Optionally an antioxidant from 0.01 to 1 wt % with respect to the total weight.

In one embodiment of the present invention, the therapeutically effective dose of mirabegron is 25 mg or 50 mg.

The present invention further relates to a tablet composition as described hereinabove, prepared by granulation process. Granulation can be performed by a wet or dry process, wherein wet granulation using water or organic solvents or mixtures thereof as granulation liquid and dry granulation can be performed by processes known as slugging or roller compaction. Preferably, the granules of the present invention have a particle size distribution $D_{90}$ equal or less than 1 mm.

In a preferred embodiment the granules of the present invention are prepared by a wet-granulation process comprising the steps:

1. Granulating mirabegron, polyethylene oxide, the water insoluble hydrophilic substance and optionally an antioxidant with a solvent to form a granulate;
2. Drying the resulting granulate;
3. Further mixing the obtained granulate with polyethylene oxide and one or more further pharmaceutically acceptable excipients to form a further mixture;
4. Compressing the mixture obtained in step (3) into a tablet; and optionally;
5. Coating the tablet.

In a preferred embodiment the solvent of step 1 is an ethanol/water solvent or ethanol. Ethanol 96% is preferred.

The pharmaceutical compositions described herein can be made using conventional methods and equipment well-known in the art.

The pharmaceutical (tablet) compositions of the present invention show an in vitro dissolution profile wherein mirabegron is released at least 10%, preferably 10-50% within 3 hours, at least 30%, preferably 30-70% within 5 hours and at least 80% within 10 hours when the composition is subjected to a dissolution study in 900 ml phosphate buffer (pH 6.8) using a USP apparatus 1 (basket) at 100 rpm at 37° C.

The pharmaceutical composition of the present invention can be used in combination with another API to form multilayer tablets. A preferred API to use in combination with is solifenacin.

The present invention is illustrated by the following Examples.

Examples

TABLE 1

Qualitative and quantitative formula example 1

| Components | mg/tablet | % |
|---|---|---|
| Intragranular | | |
| Mirabegron | 50.000 | 20.0 |
| PEO 2,000,000 (Polyox WSR N60K) | 35.000 | 14.0 |
| Microcrystalline cellulose (Vivapur 101) | 63.750 | 25.5 |
| Extragranular | | |
| PEO 900,000 (Polyox WSR 1105) | 35.000 | 14.0 |
| Microcrystalline cellulose (Vivapur 102) | 63.750 | 25.5 |
| Magnesium stearate | 2.500 | 1.0 |
| Ethanol:water (85:15) | qs | qs |
| Core weight | 250.000 | 100.0 |
| Opadry Yellow 03F220071 | 7.500 | — |
| Final weight | 257.500 | |

TABLE 2

Qualitative and quantitative formula example 2

| Components | mg/tablet | % |
|---|---|---|
| Intragranular | | |
| Mirabegron | 50.000 | 20.0 |
| PEO 2,000,000 (Polyox WSR N60K) | 35.000 | 14.0 |
| Microcrystalline cellulose (Vivapur 101) | 127.500 | 51.0 |
| Extragranular | | |
| PEO 900,000 (Polyox WSR 1105) | 35.000 | 14.0 |
| Magnesium stearate | 2.500 | 1.0 |
| Ethanol:water (85:15) | qs | qs |
| Core weight | 250.000 | 100.0 |
| Opadry Yellow 03F220071 | 7.500 | — |
| Final weight | 257.500 | |

TABLE 3

Qualitative and quantitative formula example 3

| Components | mg/tablet | % |
|---|---|---|
| Intragranular | | |
| Mirabegron | 50.000 | 20.0 |
| PEO 2,000,000 (Polyox WSR N60K) | 25.000 | 10.0 |
| Microcrystalline cellulose (Vivapur 101) | 127.500 | 51.0 |
| Extragranular | | |
| PEO 900,000 (Polyox WSR 1105) | 45.000 | 18.0 |
| Magnesium stearate | 2.500 | 1.0 |
| Ethanol:water (85:15) | qs | qs |
| Core weight | 250.000 | 100.00 |
| Opadry Yellow 03F220071 | 7.500 | — |
| Final weight | 257.500 | |

TABLE 4

Qualitative and quantitative formula example 4

| Components | mg/tablet | % |
|---|---|---|
| Intragranular | | |
| Mirabegron | 50.000 | 20.00 |
| PEO 2,000,000 (Polyox WSR N60K) | 2.500 | 1.00 |
| Microcrystalline cellulose (Vivapur 101) | 149.600 | 59.84 |
| BHT | 0.400 | 0.16 |
| Ethanol 96% | qs | qs |

TABLE 4-continued

Qualitative and quantitative formula example 4

| Components | mg/tablet | % |
|---|---|---|
| Extragranular | | |
| PEO 900,000 (Polyox WSR 1105) | 45.000 | 18.00 |
| Magnesium stearate | 2.500 | 1.00 |
| Core weight | 250.000 | 100.00 |
| Opadry Yellow 03F220071 | 7.500 | — |
| Final weight | 257.500 | |

TABLE 5

Qualitative and quantitative formula example 5

| Components | mg/tablet | % |
|---|---|---|
| Intragranular | | |
| Mirabegron | 50.000 | 20.00 |
| PEO 2,000,000 (Polyox WSR N60K) | 5.000 | 2.00 |
| Microcrystalline cellulose (Vivapur 101) | 147.100 | 58.84 |
| BHT | 0.400 | 0.16 |
| Ethanol 96% | q.s. | q.s. |
| Extragranular | | |
| PEO 900,000 (Polyox WSR 1105) | 45.000 | 18.00 |
| Magnesium stearate | 2.500 | 1.00 |
| Core weight | 250.000 | 100.00 |
| Opadry Yellow 03F220071 | 7.500 | — |
| Final weight | 257.500 | |

Figure 2:
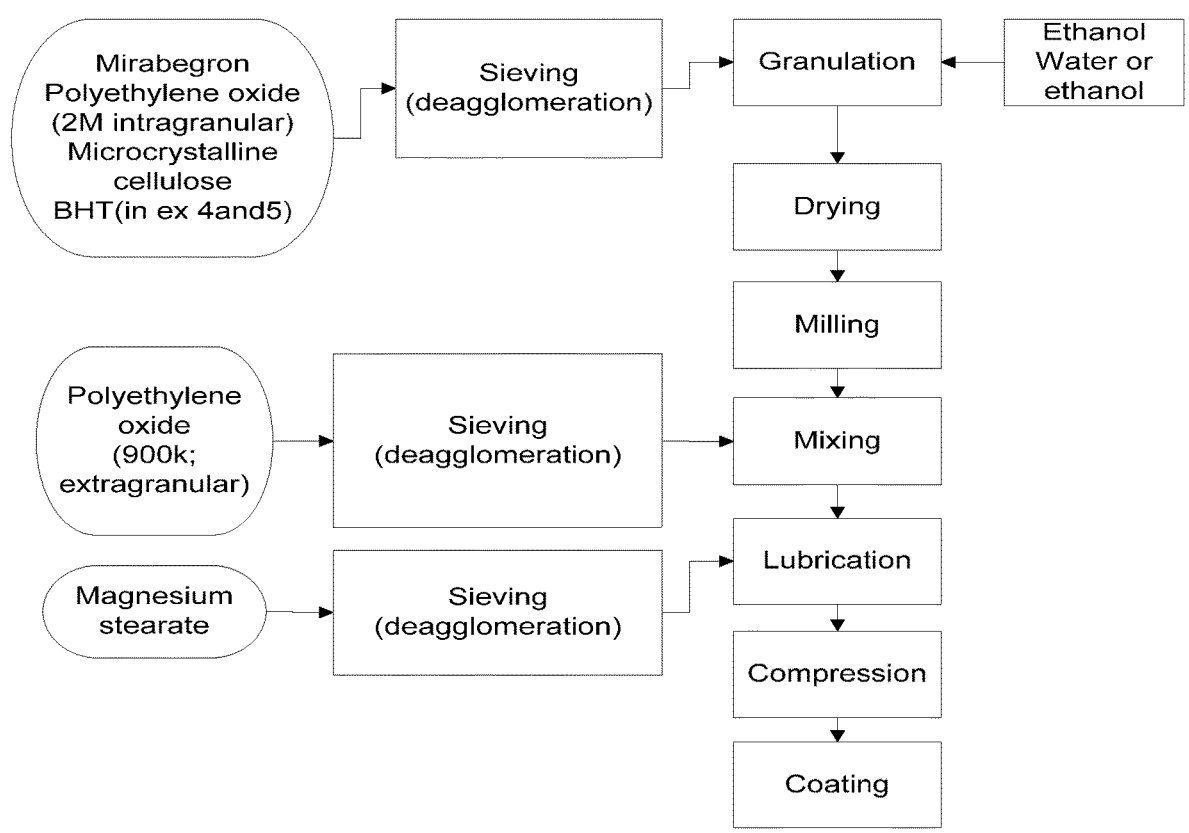
FIG. 2 shows the process for making the tablets of examples 1-5.

The tablets of Example 1, 2, 3, 4 and 5 were made according to the process depicted in FIG. 2.

FIG. 1 shows the in vitro dissolution profiles of 50 mg mirabegron modified release tablets in accordance with the present invention as compared to commercially available Betmiga® and Mirbetriq® 50 mg tablets.

The invention claimed is:

1. A modified release tablet composition comprising:
   5 to 25 wt %, relative to the total weight, of a therapeutically effective dose of mirabegron or a pharmaceutically acceptable salt thereof;
   15 to 40 wt %, relative to the total weight, of a polyethylene oxide component that consists of one or more polyethylene oxides, the polyethylene oxide component having a viscosity of 100 to 800 cps at a 2% aqueous solution at 25° C.; and
   40 to 70 wt %, relative to the total weight, of a water insoluble hydrophilic excipient.

2. A modified release tablet composition according to claim 1 wherein the polyethylene oxide component is a mixture of a polyethylene oxide having an average molecular weight of approximately 2,000,000 and a polyethylene oxide having an average molecular weight of approximately 900,000.

3. A modified release tablet composition according to claim 2 wherein the polyethylene oxide 2,000,000 is present in a weight percentage of 1 to 15% relative to the total weight and the polyethylene oxide 900,000 is present in a weight percentage of 10 to 25% relative to the total weight.

4. A modified release tablet composition according to claim 1 wherein the water insoluble hydrophilic excipient is microcrystalline cellulose.

5. A modified release tablet composition according to claim 1 wherein mirabegron has a particle size distribution of D90 between 10 and 150 µm.

6. A modified release tablet composition according to claim 1 prepared by wet granulation or dry-granulation.

7. A modified release tablet composition according to claim 1 prepared by a wet-granulation process, which process comprises:
   (a) granulating the mirabegron, polyethylene oxide, the water insoluble hydrophilic substance and optionally antioxidant with a solvent to form a granulate;
   (b) drying the resulting granulate;
   (c) further mixing the obtained granulate with polyethylene oxide and one or more further pharmaceutically acceptable excipients to form a further mixture;
   (d) compressing the further mixture obtained in step (c) into a tablet; and
   (e) optionally coating the tablet.

8. A modified release tablet composition according to claim 7, wherein the solvent of step (a) is an alcohol.

9. A modified release tablet composition according to claim 7 wherein the granules have a particle size distribution $D_{90}$ equal or less than 1 mm.

10. A multilayer tablet comprising the modified release tablet composition according to claim 1.

11. The multilayer tablet according to claim 10, which is a bilayer tablet.

12. The multilayer tablet according to claim 10 further comprising solifenacin.

13. A modified release tablet composition according to claim 1 wherein the water insoluble hydrophilic excipient is present in a weight percentage of 45 to 65% relative to the total weight.

14. A modified release tablet composition according to claim 13 wherein the water insoluble hydrophilic excipient is microcrystalline cellulose.

15. A modified release tablet composition according to claim 1 wherein the water insoluble hydrophilic excipient is selected from the group consisting of microcrystalline cellulose, crospovidone, and croscarmellose.

16. A modified release tablet composition according to claim 3 wherein the water insoluble hydrophilic excipient is microcrystalline cellulose.

* * * * *